US008778170B2

(12) United States Patent
Long et al.

(10) Patent No.: US 8,778,170 B2
(45) Date of Patent: Jul. 15, 2014

(54) PROCESS FOR PRODUCING LIGHT OLEFINS AND AROMATICS (75) Inventors: Jun Long, Beijing (CN); Zhijian Da, Beijing (CN); Dadong Li, Beijing (CN); Xieqing Wang, Beijing (CN); Xingtian Shu, Beijing (CN); Jiushun Zhang, Beijing (CN); Hong Nie, Beijing (CN); Chaogang Xie, Beijing (CN); Zhigang Zhang, Beijing (CN); Wei Wang, Beijing (CN)

(73) Assignees: China Petroleum Chemical Corporation, Beijing (CN); Research Institute of Petroleum Processing Sinopec, Beijing (CN)

( * ) Notice: Subject to any disclaimer, the term of this patent is extended or adjusted under 35 U.S.C. 154(b) by 1965 days.

(21) Appl. No.: 10/592,166

(22) PCT Filed: Mar. 8, 2005

(86) PCT No.: PCT/CN2005/000281
§ 371 (c)(1),
(2), (4) Date: Jul. 15, 2009

(87) PCT Pub. No.: WO2005/085391
PCT Pub. Date: Sep. 15, 2005

(65) Prior Publication Data
US 2009/0288985 A1 Nov. 26, 2009

(30) Foreign Application Priority Data

Mar. 8, 2004 (CN) .......................... 2004 1 0006189
Jul. 14, 2004 (CN) .......................... 2004 1 0068934

(51) Int. Cl.
C10G 51/02 (2006.01)
C10G 51/04 (2006.01)

(52) U.S. Cl.
USPC .................. 208/75; 208/72; 208/73; 208/74; 585/650; 585/651

(58) Field of Classification Search
USPC ........... 208/49, 58, 61, 67, 72, 73, 78, 89, 96, 208/75, 74; 585/649, 650, 651, 653
See application file for complete search history.

(56) References Cited

U.S. PATENT DOCUMENTS 3,894,934 A * 7/1975 Owen et al. ...................... 208/78
3,928,172 A 12/1975 David, Jr. et al.
(Continued)

FOREIGN PATENT DOCUMENTS

| CN | 1215041 A | 4/1999 |
|---|---|---|
| CN | 1217366 A | 5/1999 |
| CN | 1490383 A | 4/2004 |
| DE | 287948 A | 3/1991 |

(Continued)

OTHER PUBLICATIONS

International Search Report, dated Jun. 16, 2005.
(Continued)

Primary Examiner — Renee E Robinson
(74) Attorney, Agent, or Firm — Novick, Kim & Lee, PLLC; Allen Xue (57) ABSTRACT

A process for producing light olefins and aromatics, which comprises reacting a feedstock with a catalytic cracking catalyst in at least two reaction zones, wherein the reaction temperature of at least one reaction zone downstream of the first reaction zone is higher than that of the first reaction zone and its weight hourly space velocity is lower than that of the first reaction zone. The spent catalyst is separated, from the reaction product vapor, regenerated, and then returned to the reactor. The reaction product vapor is separated to obtain the desired products, light olefins and aromatics. This process efficiently produces light olefins such as propylene, ethylene, etc from heavy feedstocks, wherein the yield of propylene exceeds 20% by weight, and produces aromatics such as toluene, xylene, etc at the same time.

21 Claims, 4 Drawing Sheets

(56) References Cited

U.S. PATENT DOCUMENTS

| | | |
|---|---|---|
| 4,090,948 A | 5/1978 | Schwarzenbek |
| 4,218,306 A | 8/1980 | Gross et al. |
| 4,980,053 A | 12/1990 | Li |
| 5,154,818 A | 10/1992 | Harandi et al. |
| 5,582,714 A | 12/1996 | Forte |
| 5,685,972 A | 11/1997 | Timken et al. |
| 5,773,676 A * | 6/1998 | Drake et al. ............... 585/322 |
| 6,113,776 A | 9/2000 | Upson |
| 6,123,830 A | 9/2000 | Gupta et al. |
| 6,149,800 A | 11/2000 | Iaccino et al. |

FOREIGN PATENT DOCUMENTS

| | | | |
|---|---|---|---|
| EP | 0325437 | 7/1989 | |
| EP | 381 870 * | 8/1990 | ............ C10G 11/18 |
| JP | 10046160 A | 2/1998 | |
| JP | 2002-504169 A | 2/2002 | |
| KR | 100253887 | 4/2000 | |
| WO | WO 98/56873 * | 12/1998 | ............ C10G 11/00 |
| WO | WO 00/31215 | 6/2000 | |

OTHER PUBLICATIONS

Supplementary European Search Report dated Feb. 27, 2012.

\* cited by examiner

PROCESS FOR PRODUCING LIGHT OLEFINS AND AROMATICS

RELATED APPLICATIONS

This application is the National Stage application of PCT/CN2005/000281, filed Mar. 8, 2005, which claims priority to Chinese Application No. 200410006189, filed Mar. 8, 2004 and Chinese Application No. 200410068934.5 filed on Jul. 14, 2004.

FIELD OF THE INVENTION

The present invention pertains to a process for the catalytic conversion of hydrocarbon oils in the absence of hydrogen and, more particularly, it pertains to a process for converting heavy feedstocks into light olefins rich in propylene and ethylene and aromatics rich in toluene and xylene.

BACKGROUND OF THE INVENTION

Light olefins such as ethylene, propylene, etc are important chemical feedstocks, wherein propylene is a synthetic monomer of the products such as polypropylene, acrylonitrile, etc. Along with the rapid increase of the demand for the derivatives such as polypropylene, etc, the demand for propylene is also rapidly increasing year by year. The demand of the world market for propylene already increased from 15.2 million tons of 20 years ago to 51.2 million tons of 2000 with an average annual increase rate of 6.3%. It is predicted that the demand for propylene will have attained 86 million tons by 2010 with an average annual increase rate of 5.6%.

The process for producing propylene is mainly steam cracking and catalytic cracking (FCC), wherein steam cracking uses light oils such as naphtha, etc. as feedstocks to produce ethylene and propylene by thermal cracking with a propylene yield of only about 15% by weight, while FCC uses heavy oils such as vacuum gas oil (VGO) as a feedstock. Presently, 66% propylene in the world comes from the byproducts of steam cracking for producing ethylene, 32% comes from the byproducts of FCC of refineries for producing naphtha and diesel, and a small amount (about 2%) is obtained from the dehydrogenation of propane and metathesis of between ethylene and butene.

If the petrochemical industry produces ethylene and propylene through the conventional steam cracking route, several restrictive factors would be faced such as shortage of light feedstocks, deficiency of the processing capacity, and high production cost.

FCC is drawing increasing attention due to its advantages of wide adaptability, flexible operation, etc. In the United States of America, almost 50% of the demand of the market for propylene comes from FCC units. The development of the improved techniques of catalytic cracking for increasing the production of propylene is very rapid.

U.S. Pat. No. 4,980,053 discloses a conversion process for producing light olefins from hydrocarbons, wherein the feedstocks are petroleum fractions, residuum, or crude oil with different boiling ranges and the converting reaction is carried out in a fluidized bed or moving bed reactor under the conditions of a temperature between 500° C. and 650 C, a pressure between $1.5 \times 10^5$ and $3 \times 10^5$ Pa, a WHSV between $0.2 \text{ h}^{-1}$ and $2.0 \text{ h}^{-1}$, and a catalyst to oil ratio between 2 and 12 by using a solid acid catalyst. The catalyst returns to the reactor for cycle use after being regenerated by burning off coke. By this process, the total yield of propylene and ethylene may attain about 40%, wherein the yield of propylene is up to 26.34%.

WO 00/31215A1 discloses a catalytic cracking process for producing olefins, which uses a catalyst with ZSM-5 and/or ZSM-11 zeolites as active components and a great amount of inert substances as substrates, and uses VGO as a feedstock. The yield of propylene does not exceed 20% by weight.

U.S. Pat. No. 6,123,830 discloses a combination process consisting of two-stage catalytic cracking and two-stage hydrotreating, the objective of which is to produce as much olefins as possible and improve the quality of oil distillates and octane number of naphtha. The feedstock is converted into the first hydrotreated product in the first hydrotreating unit, and the first hydrotreated product enters the first catalytic cracking unit, wherein naphtha, diesel, and heavy oil are obtained by using a catalyst with an intermediate pore size zeolite as a main active component. The heavy oil enters the second hydrotreating unit for hydrogenation to obtain the second hydrotreated product, and the second hydrotreated product enters the second catalytic cracking unit for cracking, wherein the active component of the catalyst is mainly an intermediate pore size zeolite. The yield of propylene in this process is rather low.

Aromatics are also important chemical feedstocks, in particular, light aromatics such as BTX (benzene, toluene, and xylene), which are used to produce synthetic materials such as chemical fibers, plastics, etc. Presently, the major process for producing aromatics is catalytic reforming, wherein the feedstock is fed to strict pretreatment because the active components of the reforming catalyst are noble metals. Disadvantageously, the process flow of the movement and regeneration of the reforming catalyst is complicated.

The above references produce propylene only as a byproduct with low yields not exceeding 30% and at the same time that naphtha and diesel are produced. Several of the references only can produce aromatics, but cannot produce light olefins and aromatics simultaneously. In order to meet the increasing demand for the chemical feedstocks, propylene, ethylene, aromatics, etc, there is a necessity to develop a chemical industry type oil refining process for simultaneously producing large amounts of propylene, ethylene, and aromatics from heavy feedstocks.

SUMMARY OF THE INVENTION

The objective of the present invention is to provide several processes for simultaneously producing propylene, ethylene, and aromatics from heavy feedstocks, the yield of propylene in these processes being higher than 20%.

Technical Scheme 1

In one aspect, the process for producing light olefins and aromatics includes a feedstock that comes into contact with a catalytic cracking catalyst and reacts under the conditions of a reaction temperature between 400° C. and 800° C., and a WHSV between $0.1 \text{ h}^{-1}$ and $750 \text{ h}^{-1}$. The reaction is carried out in at least two reaction zones, and the reaction temperature of at least one reaction zone among the reaction zones at the down stream side of the first reaction zone is higher than that of the first reaction zone and its WHSV is lower than that of the first reaction zone. Spent catalyst is separated from the reaction product vapor and the catalyst returns to the reactor after being regenerated. The reaction product vapor is separated to obtain the desired products, light olefins and aromatics.

Technical Scheme 2

In another aspect, the process for producing light olefins and aromatics includes a first step of feeding a feedstock and an optional cycle material into a hydrotreating unit for contact with a hydrotreating catalyst and hydrogen, and reaction under the conditions of a hydrogen partial pressure between 3.0 MPa and 20.0 MPa, a reaction temperature between 300° C. and 450° C., a hydrogen/oil ratio between 300 and 2000 by volume, and a LHSV between 0.1 h$^{-1}$ and 3.0 h$^{-1}$. The reaction effluent is then separated to obtain hydrotreated product, with hydrogen being cycled for reuse. In a second step, the hydrotreated product is reacted with a catalytic cracking catalyst under the conditions of a reaction temperature between 400° C. and 800° C., and a WHSV between 0.1 h$^{-1}$ and 750 h$^{-1}$. The reaction is carried out in at least two reaction zones, and the reaction temperature of at least one reaction zone among the reaction zones at the down stream side of the first reaction zone is higher than that of the first reaction zone and its WHSV is lower than that of the first reaction zone. The spent catalyst is separated from the reaction product vapor and the catalyst returns to the reactor after being regenerated. The reaction product vapor is separated to obtain desired products, light olefins and aromatics.

Technical Scheme 3

In another aspect, the process for producing light olefins and aromatics includes a first step of contacting a feedstock with hydrogen for reaction with a hydrotreating catalyst under the conditions of a hydrogen partial pressure between 3.0 MPa and 20.0 MPa, a reaction temperature between 300° C. and 450° C., a hydrogen/oil ratio between 300 and 2000 by volume, and a LHSV between 0.1 h$^{-1}$-3.0 h$^{-1}$. The reaction effluent is then separated to obtain H$_2$, CH$_4$, hydrotreated C$_2^0$-C$_4^0$, hydrotreated naphtha, and hydrotreated product, with hydrogen being cycled for reuse. In a second step, the hydrotreated product of the first step is reacted with a catalytic cracking catalyst under the conditions of a reaction temperature between 400° C. and 800° C. and a WHSV between 0.1 h$^{-1}$-750 h$^{-1}$. The reaction is carried out in at least two reaction zones, and the reaction temperature of at least one reaction zone among the reaction zones at the down stream side of the first reaction zone is higher than that of the first reaction zone and its WHSV is lower than that of the first reaction zone. The spent catalyst is separated from the reaction product vapor and returns to all or a part of the reaction zones of step (2) after being stripped and regenerated. The reaction product vapor is separated to obtain H$_2$, CH$_4$, catalytic cracking C$_2^=$-C$_3^=$, catalytic cracking C$_2^0$-C$_3^0$, catalytic cracking C$_4$-C$_5$, catalytic cracking naphtha, LCO, and heavy cycle oil, wherein C$_2^=$-C$_3^=$ are a part of the desired products and catalytic cracking C$_4$-C$_5$ are cycled back to the catalytic cracking reactor.

In a third step, the hydrotreated C$_2^0$-C$_4^0$ and hydrotreated naphtha of the first step and catalytic cracking C$_2^0$-C$_3^0$ of the second step are treated with steam under a temperature between 700° C.-1000° C., and the reaction product vapor is separated to obtain H$_2$, CH$_4$, steam cracking C$_2^=$-C$_3^=$, steam cracking C$_2^0$-C$_3^0$, steam cracking C$_4$-C$_5$, steam cracking naphtha, and fuel oil, wherein the steam cracking C$_2^=$-C$_3^=$ are a part of the desired products and the steam cracking C$_4$-C$_5$ are cycled back to the catalytic cracking reactor.

In a fourth step, the catalytic cracking naphtha of the second step and steam cracking naphtha of the third step are selectively hydrogenated, and then fed to solvent extraction to obtain aromatics and extraction raffinate, wherein the aromatics are a part of the desired products, and the extraction raffinate returns to the third step as one of the feedstocks of the steam cracking.

In one example, an apparatus for producing light olefins and aromatics includes a hydrotreating unit, wherein H$_2$, CH$_4$, hydrotreated C$_2^0$-C$_4^0$, hydrotreated naphtha, and hydrotreated product are obtained after a feedstock comes into contact with hydrogen and a hydrotreating catalyst. A catalytic cracking unit for reacting the hydrotreated product with a catalytic cracking catalyst. The reaction is carried out in at least two reaction zones, and the reaction temperature of at least one reaction zone among the reaction zones downstream of the first reaction zone is higher than that of the first reaction zone and its WHSV is lower than that of the first reaction zone. The spent catalyst is separated from the reaction product vapor, wherein the catalyst returns to all or a part of the reaction zones of the second step from above after being stripped and regenerated, and the reaction product vapor is separated to obtain H$_2$, CH$_4$, catalytic cracking C$_2^=$-C$_3^=$, catalytic cracking C$_2^0$-C$_3^0$, catalytic cracking C$_4$-C$_5$, catalytic cracking naphtha, LCO, and HCO. The C$_2^=$-C$_3^=$ are a part of the desired products, and the catalytic cracking C$_4$-C$_5$ are cycled back to the catalytic cracking reactor. A steam cracking unit for reacting the hydrotreated C$_2^0$-C$_4^0$, hydrotreated naphtha, and catalytic cracking C$_2^0$-C$_3^0$ with steam under a temperature between 700° C. and 1000° C. and the reaction product vapor is separated to obtain H$_2$, CH$_4$, steam cracking C$_2^=$-C$_3^=$, steam cracking C$_2^0$-C$_3^0$, steam cracking C$_4$-C$_5$, steam cracking naphtha, and fuel oil, wherein the steam cracking C$_2^=$-C$_3^=$ are a part of the desired products. A selective hydrogenation unit for selectively hydrogenating the catalytic cracking naphtha and the steam cracking naphtha to obtain the selectively hydrotreated naphtha;

(1) A solvent extraction unit for selectively extracting hydrotreated naphtha to obtain aromatics and extraction raffinate. The aromatics are a part of the desired products, and the extraction raffinate returns to the steam cracking unit as one of the feedstocks for steam cracking.

These and other features of the present invention can be best understood from the following specification and drawings, the following of which is a brief description.

DETAILED DESCRIPTION OF THE PREFERRED EMBODIMENT

In one example, a process for producing light olefins and aromatics includes a feedstock that comes into contact with a catalytic cracking catalyst and reacts under a reaction temperature between 400° C. and 800° C., and a WHSV between 0.1 h$^{-1}$ and 750 h$^{-1}$. The reaction is carried out in at least two reaction zones, and the reaction temperature of at least one reaction zone among the reaction zones downstream of the first reaction zone is higher than that of the first reaction zone and its WHSV is lower than that of the first reaction zone. Spent catalyst is separated from the reaction product vapor and the catalyst returns to the reactor after being regenerated. The reaction product vapor is separated to obtain the desired products, light olefins and aromatics.

1) Feedstock

In one particular example, the feedstocks in each reaction zone are petroleum hydrocarbons, other mineral oils, or both, wherein the petroleum hydrocarbon is one selected from the group consisting of vacuum gas oil (VGO), atmospheric gas oil (AGO), coked gas oil (CGO), deasphalted oil (DAO), vacuum residuum (VR), atmospheric residuum (AR), cycle oil, slurry, diesel, naphtha, hydrocarbons with 4-8 carbon atoms, alkanes with 2-3 carbon atoms, or mixtures thereof and the other mineral oil is liquid products from coal liquefaction, tar sand oil, or shale oil.

In one example, the feedstock of the first reaction zone is one selected from the group consisting of vacuum gas oil, atmospheric gas oil, coked gas oil, deasphalted oil, vacuum residuum, atmospheric residuumn, cycle oil, slurry, diesel, naphtha or mixture thereof. The feed of reaction zones downstream of the first reaction zone is one selected from the group consisting of cycle oil, slurry, diesel, naphtha, hydrocarbons with 4-8 carbon atoms, alkanes with 2-3 carbon atoms or mixture thereof. The VGO, AGO, CGO, DAO, VR, AR, diesel, and naphtha are unhydrotreated or hydrotreated whole fraction or partial fraction. The naphtha is one selected from catalytic cracking naphtha, catalytic cracking naphtha, straight-run naphtha, coked naphtha, steam cracking naphtha, thermal cracking naphtha, and hydrotreated naphtha, or mixtures thereof, wherein catalytic cracking naphtha may be either from the catalytic cracking process of the present invention, or from conventional catalytic cracking, straight-run naphtha, coked naphtha, steam cracking naphtha, thermal cracking naphtha, and hydrotreated naphtha are from outside of the present process. The diesel is one selected from catalytic cracking LCO, straight-run diesel, coked diesel, thermal cracking diesel, and hydrotreated diesel obtained by the present process, or mixtures thereof, wherein catalytic cracking LCO may be either from the catalytic cracking process of the present invention, or from conventional catalytic cracking, straight-run diesel, coked diesel, thermal cracking diesel, and hydrotreated diesel are from outside of the present process.

The hydrocarbons with 4-8 carbon atoms and alkanes with 2-3 carbon atoms can be either from the catalytic cracking process of the present invention, or from conventional catalytic cracking, coking, thermal cracking, hydrogenating, etc. processes.

The feedstock of each reaction zone may be identical, or different. In one example, the feedstock of the first reaction zone is a heavier hydrocarbon, such as VGO, AGO, CGO, DAO, VR, AR, self-produced cycle oil, self-produced slurry, outside cycle oil, outside slurry, diesel, and naphtha. The reaction zone with higher reaction temperature is a lighter hydrocarbon, such as hydrocarbons with 4-8 carbon atoms, alkanes with 2-3 carbon atoms, naphtha, and diesel.

2) Catalytic Cracking Catalyst

In this example, the catalytic cracking catalyst comprises zeolite, inorganic oxide, and optionally, clay, which accounts for the following percent of the total weight of the catalyst, respectively: about 10%-50% zeolite by weight, about 5%-90% inorganic oxide by weight, and about 0%-70% clay by weight. The term "about" as used in this description relative to percentages or compositions refers to possible variation in the compositional percentages, such as normally accepted variations or tolerances in the art.

The zeolite is an active component, which is selected from intermediate pore size zeolite, and optionally, large pore zeolite. In one example, he intermediate pore size zeolite accounts for about 25%-100%, preferably about 50%-100% of the total weight of the zeolite and the large pore zeolite accounts for about 0%-75%, preferably about 0%-50% of the total weight of the zeolite. The intermediate pore size zeolite is selected from ZSM series zeolites and/or ZRP zeolites, or ZSM and ZRP zeolites modified with nonmetal elements such as phosphor and/or transition metal elements such as iron, cobalt, and nickel. U.S. Pat. No. 5,232,675 discloses further description of ZRP zeolites. The ZSM series zeolite is one selected from the group consisting of ZSM-5, ZSM-11, ZSM-12, ZSM-23, ZSM-35, ZSM-38, and ZSM-48, and other zeolites with similar structure, or mixtures thereof. U.S. Pat. No. 3,702,886 discloses further description of ZSM-5 zeolites. In this example, the large pore zeolite is one selected from the group consisting of rare-earth Y (REY), rare-earth HY (REHY), ultrastable Y and high silica Y obtained by different processes or mixtures thereof.

The inorganic oxide as a binder is selected from silica ($SiO_2$) and/or alumina ($Al_2O_3$).

Clay as a matrix (i.e. supporter) is selected from kaolin and/or halloysite.

The catalytic cracking catalyst in each reactor may be identical or different.

3) Catalytic Cracking Reactor

The cracking reactor comprises at least two, preferably 2-7, and more preferably 2-3 reaction zones. Each reaction zone is one selected from riser, fluidized bed, ascending transfer line, descending transfer line, and moving bed or some part thereof. The connections between the various reaction zones are series, parallel, or series-parallel. The riser can be the conventional unidiameter, or various types of tapered risers. The structure and dimension of each reaction zone may be identical or different, wherein the velocity of the gas in the fluidized bed is between about 0.1 m/s and 2.4 m/s (catalyst is neglected).

In this example, the first reaction zone is a zone wherein a feedstock with a boiling range between about 25° C. and 1200° C. comes into contact with the catalyst. The feedstock for the first reaction zone may also be a feedstock of the conventional catalytic cracking wherein a small amount of light hydrocarbons with boiling points lower than those of the feedstock of the conventional catalytic cracking, such as $C_2$-$C_6$, may be incorporated. There may be other reaction zones upstream side of this reaction zone. The feedstock of the conventional catalytic cracking is one selected from the group consisting of vacuum gas oil, atmospheric gas oil, coked gas oil, deasphalted oil, vacuum residuum, atmospheric residuum, cycle oil, slurry, diesel, naphtha or mixture thereof.

The first reaction zone is preferably riser, ascending transfer line, descending transfer line, or fluidized bed, and more preferably riser or fluidized bed. The other reaction zone is preferably fluidized bed, riser, or moving bed, and more preferably fluidized bed or riser.

4) Operating Conditions

In one example, the operating conditions include a reaction temperature of about 400° C.-800° C., preferably about 500° C.-700° C., a WHSV of about 0.1 $h^{-1}$-750 $h^{-1}$, preferably about 1 $h^{-1}$-500 $h^{-1}$, a reaction pressure of about 0.10 MPa-1.0 MPa (absolute pressure), and a ratio of catalytic cracking catalyst to feedstock about 1-150 by weight. According to the common knowledge of the ordinary in the art, the reaction temperature of a tube reactor such as riser reactor means the outlet temperature, and the reaction temperature of a bed reactor such as fluidized bed reactor means the average temperature of the bed.

In order to realize the fluidized operation, a lifting medium may be injected from the bottom of the reaction zone and the lifting medium is selected from steam or dry gas with steam being preferred. The ratio of steam to the feedstock is about 0.05-1.0 by weight.

The reaction temperature of at least one, preferably 1-6, and more preferably 1-2 reaction zones out of the reaction zones downstream of the first reaction zone is higher than that of the first reaction zone. The difference between the reaction temperature of the reaction zone with a higher reaction temperature and that of the first reaction zone is about 10° C.-200° C., preferably about 20° C.-100° C.

In order that the reaction temperature of at least one reaction zone out of the reaction zones downstream of the first reaction zone is higher than that of the first reaction zone, heat is supplemented to the above reaction zone by means of one or more of the ways selected form supplying hot regenerated catalyst, hot coke deposited catalyst, hot fresh catalyst, and hot feedstock to the reaction zone, or equipping heating coil pipes in the reaction zone. The total heat supplemented accounts for about 10%-80%, and preferably about 20%-60%, of the reaction heat of the total reaction system.

The WHSV of at least one, preferably 1-6, and more preferably 1-2 reaction zones out of the reaction zones downstream of the first reaction zone is lower than that of the first reaction zone, and ratio of the WHSV of this reaction zone to that of the first reaction zone is about 1:1.1-1:750, and preferably about 1:1.1-1:300.

The spent catalyst is separated from reaction product vapor by conventional disengaging, cyclone separation and the catalyst returns to the reactor after being regenerated by burning off coke, before which the catalyst is optionally fed to stripping.

5) Separation of the Product

The product includes light olefins, such as ethylene, propylene, and optionally, butene.

The process for separating ethylene from the reaction product vapor is the same as that for separating ethylene, which is well known to the ordinary skilled in the art, and the process for separating propylene, and optionally, butene from the reaction product vapor is the same as that for separating propylene and butene, which is well known to the ordinary skilled in the art. The process for separating aromatics from the cracking naphtha fraction of the reaction product vapor is the same as that for separating aromatics, which is well known to the ordinary skilled in the art, i.e. extraction. Before separating aromatics from the catalytic cracking naphtha obtained by the present process, $C_5$-$C_8$ in this naphtha may be separated first as a recycle stream.

An example technical scheme for separating the product includes the following steps.

(1) The feedstock and steam enters the first reaction zone, i.e. the riser, come into contact with a regenerated, fresh catalytic cracking catalyst, or both, and reacts under the conditions of a reaction temperature between about 500° C. and 700° C., a WHSV between about 0.1 $h^{-1}$ and 750 $h^{-1}$, a reaction pressure between about 0.1 Mpa and 1.0 Mpa (absolute pressure), a ratio of the catalytic cracking catalyst to the feedstock between about 1 and 150 by weight, and a ratio of steam to the feedstock between about 0.05 and 1.0 by weight.

(2) The reaction effluent from the first reaction zone enters the second reaction zone, i.e. the fluidized bed, comes into contact with the regenerated catalytic cracking catalyst, steam, ethane, propane, $C_4$-$C_8$, and reacts under conditions of a reaction temperature between about 500° C. and 700° C., a WHSV between about 0.1 brand 750 $h^{-1}$, a reaction pressure between about 0.1 Mpa and 1.0 Mpa (absolute pressure), a ratio of the catalytic cracking catalyst to feedstock between about 1 and 150 by weight, and a ratio of steam to feedstock between about 0.05 and 1.0 by weight. The difference between the reaction temperature of the second reaction zone and that of the first reaction zone is about 10° C.-200° C., preferably about 20° C.-100° C. The ratio of the WHSV of the second reaction zone to that of the first reaction zone is about 1:1.1-1:750, preferably about 1:1.1-1:300;

(3) The spent catalyst in the second reaction zone is separated from the reaction product vapor. The spent catalyst enters the regenerator after stripping and returns to the first reaction zone and the second reaction zone after being regenerated by burning off coke, and the reaction product vapor is separated to obtain the desired products, light olefins and aromatics.

Optionally, a step (4) includes recycling remaining gases and liquids in the reaction gas-oil except the desired products, $H_2$ and $CH_4$ as recycle streams, which comprise ethane, propane, and $C_4$-$C_6$. The extraction raffinate obtained after the solvent extraction of the naphtha returns to the second reaction zone, and the diesel, cycle oil, and slurry return to the first reaction zone.

Embodiment 2

Another example process for producing light olefins and aromatics includes the following steps.

(1) A feedstock, and optionally a recycle stream, enter the hydrotreating unit and react with a hydrotreating catalyst and hydrogen under the conditions of a hydrogen partial pressure between about 3.0 MPa and about 20.0 MPa, a reaction temperature between about 300° C. and about 450° C., a hydrogen/oil ratio between about 300 and 2000 by volume, and a LHSV between about 0.1 $h^{-1}$ and 3.0 $h^{-1}$. The reaction effluent is separated to obtain hydrotreated product and hydrogen is recycled for use.

(2) The hydrotreated product comes into contact with a catalytic cracking catalyst and reacts under the conditions of a reaction temperature between about 400° C. and 800° C. and a WHSV between about 0.1 $h^{-1}$-750 $h^{-1}$ in at least two reaction zones, wherein the reaction temperature of at least one reaction zone out of the reaction zones downstream of the first reaction zone is higher than that of the first reaction zone, and the WHSV of at least one reaction zone out of the reaction zones downstream of the first reaction zone is lower than that of the first reaction zone. The spent catalyst is separated from the reaction product vapor. The spent catalyst is recycled for use after being regenerated and the reaction product vapor is separated to obtain the desired products, light olefins and aromatics.

This example optionally further includes a step (3) of recycling remaining gases and liquids in the reaction gas-oil except the desired products, $H_2$ and $CH_4$, as recycle streams, wherein the gas recycle streams are ethane, propane, and $C_4$, and the liquid recycle streams are $C_5$-$C_6$, extraction raffinate of the naphtha, recycled oil, and slurry. Ethane, propane, and $C_4$-$C_6$, and/or extraction raffinate of naphtha, diesel, cycle oil, and slurry. Ethane, propane, $C_4$-$C_6$, aforesaid extraction raffinate, diesel, or hydrotreated diesel, and slurry return to the reaction zone of step (2), and the cycle oil returns to the hydrotreating unit. The lower alkanes, which do not participate in the reaction, are withdrawn from the unit.

In one example, the feedstock is petroleum hydrocarbons, other mineral oils, or both, wherein the petroleum hydrocarbon is one selected from the group consisting of VGO, AGO, CGO, DAO, VR, AR, diesel, and naphtha, or mixtures thereof, and the other mineral oil is liquid products from coal liquefaction, tar sand oil, or shale oil. The VGO, AGO, CGO, DAO, VR, AR, diesel, and naphtha are unhydrotreated or hydrotreated whole fraction or partial fraction. The naphtha is one selected from catalytic cracking naphtha, straight-run naphtha, coked naphtha, steam cracking naphtha, thermal cracking naphtha, and hydrotreated naphtha, or mixtures thereof, wherein catalytic cracking naphtha may be either from the catalytic cracking process of the present invention, or from conventional catalytic cracking, straight-run naphtha, coked naphtha, steam cracking naphtha, thermal cracking naphtha, and hydrotreated naphtha are from outside of the present process. The diesel is one selected from catalytic cracking LCO, catalytic cracking diesel, straight-run diesel, coked diesel, thermal cracking diesel, and hydrotreated diesel, or mixtures thereof, wherein catalytic cracking LCO may be either from the catalytic cracking process of the present invention, or from conventional catalytic cracking, straight-run diesel, coked diesel, thermal cracking diesel, and hydrotreated diesel are from outside of the present process.

The feedstock and cycle oil in step (1) may enter the hydrotreating reactor together after mixing to reduce the investment on the equipment. The feedstock and cycle oil come into contact with a hydrotreating catalyst and hydrogen, and reacts under the conditions of a hydrogen partial pressure between about 3.0 MPa and 20.0 MPa, a reaction temperature between about 300° C. and 450° C., a hydrogen/oil ratio between about 300 and 2000 by volume, and a LHSV between about 0.1 $h^{-1}$ and 3.0 $h^{-1}$. The reaction effluent is sequentially fed to high pressure separation, low pressure separation, and product fractionation to obtain hydrotreated product.

In a further example, the heavy oil and cycle oil are hydrotreated to obtain the optimum reaction effect, but the high pressure separation, low pressure separation, and product fractionation systems may be shared. The two reaction systems may use a same pressure level in order to share the compressors of fresh hydrogen and recycle hydrogen. The conditions in the hydrogenation of the feedstock include a hydrogen partial pressure of about 3.0 MPa-20.0 MPa, a reaction temperature of about 300° C.-450° C., a hydrogen/oil ratio of about 300-2000 by volume, and a LHSV of about 0.1 $h^{-1}$-3.0 $h^{-1}$. The conditions of the hydrotreating of the cycle oil include a hydrogen partial pressure of about 3.0 MPa-20.0 MPa, a reaction temperature of about 300° C.-450° C., a hydrogen/oil ratio of about 300-2000 by volume, and a LHSV of about 0.2 $h^{-}$-2.0 $h^{-1}$.

In one example, the hydrotreating catalyst used in the hydrotreating unit is a catalyst of the non-noble metals of Group VIB, Group VIII, or combination thereof supported on alumina, amorphous silica-alumina, or combination thereof. The non-noble metal of Group VIB is selected from Mo and W, and that of Group VIII is selected from Co and Ni. High hydrosaturation and denitrogenation activities, but a low cracking activity, are required for this catalyst to reserve long straight chain paraffins in the feedstock as much as possible and produce more propylene in catalytic cracking process. In one example, the catalyst comprises about 0-10% by weight of an additive, about 1-9% by weight of one or more of Group VIII metals, about 12-39% by weight of one or more of Group VIB metals, and the remainder % alumina, amorphous silica-alumina, or a combination thereof as support. The additive is selected from non-metal elements and metal elements, such as fluorine, phosphor, titanium, etc.

Compared with the feedstock, the hydrotreated product contains less sulfur, nitrogen, and aromatics, and a higher content of hydrogen, favorable for enhancing the yield of propylene when used as a feedstock for the catalytic cracking unit.

The catalytic cracking catalyst, catalytic cracking reactor, and catalytic cracking operating conditions of this technical scheme example are the same as those of previous examples.

Embodiment 3

Another example process for producing light olefins and aromatics includes the following steps.

(1) A feedstock reacts with hydrogen and a hydrotreating catalyst under the conditions of a hydrogen partial pressure between about 3.0 MPa and 20.0 MPa, a reaction temperature between about 300° C. and 450° C., a hydrogen/oil ratio between about 300-2000 by volume, and a LHSV between about 0.1 $h^{-1}$-3.0 $h^{-1}$. The reaction effluent is then separated to obtain $H_2$, $CH_4$, hydrotreated $C_2^0$-$C_4^0$, hydrotreated naphtha, and hydrotreated product, the hydrotreated product, hydrogen being recycled for use.

(2) The hydrotreated product of step (1) reacts with a catalytic cracking catalyst under the conditions of a reaction temperature between about 400° C. and 800° C. and a WHSV between about 0.1 $h^{-1}$-750 $h^{-1}$ in at least two reaction zones. The reaction temperature of at least one reaction zone downstream of the first reaction zone is higher than that of the first reaction zone, and the WHSV of at least one reaction zone downstream of the first reaction zone is lower than that of the first reaction zone. Spent catalyst is separated from the reaction product vapor, the spent catalyst returning to all or a part of the reaction zones of step (2) after being stripped and regenerated, and the reaction product vapor being separated to obtain $H_2$, $CH_4$, catalytic cracking $C_2^=$-$C_3^=$, catalytic cracking $C_2^0$-$C_3^0$, catalytic cracking $C_4$-$C_5$, catalytic cracking naphtha, light cycle oil, heavy cycle oil, wherein the $C_2^=$-$C_3^=$ are a part of the desired products and the catalytic cracking $C_4$-$C_5$ are recycled to the catalytic pyrolyzed reactor;

(3) The hydrotreated $C_2^0$-$C_4^0$ of step (1) and catalytic cracking $C_2^0$-$C_3^0$ of step (2) come into contact with steam under a temperature between about 700° C.-1000° C. and the reaction product vapor is separated to obtain $H_2$, $CH_4$, steam cracking $C_2^=$-$C_3^=$, steam cracking $C_2^0$-$C_3^0$, steam cracking $C_4$-$C_5$, steam cracking naphtha, fuel oil, wherein the steam cracking $C_2^=$-$C_3^=$ are a part of the desired products and the steam cracking $C_4$-$C_5$ are recycled to the catalytic cracking reactor;

(4) The catalytic cracking naphtha of step (2) and steam cracking naphtha of step (3) are selectively hydrogenated, and then fed for solvent extraction to obtain aromatics and extraction raffinate, wherein the aromatics are a part of the desired products, the extraction raffinate returning to step (3) as one of the feedstocks of steam cracking.

The feedstock, catalytic cracking catalyst, catalytic cracking reactor, and catalytic cracking operating conditions of this example are the same as those of previous examples.

The solvent used in solvent extraction is one selected from the group consisting of sulfolane, N-methyl pyrrolidone, diethyl glycol ether, triethyl glycol ether, tetraethyl glycol, dimethyl sulfoxide, and N-formyl morpholine and mixtures thereof. The temperature in solvent extraction is about 80-120° C., and the ratio of the solvent to the extracted feedstock is about 2-6 by volume. The extracted oil by solvent extraction is one of the desired products, aromatics and the extraction raffinate, i.e. non-aromatics, is one of the feedstocks for steam cracking.

The feedstocks for steam cracking are the hydrotreated $C_2^0$-$C_4^0$ and hydrotreated naphtha of step (1) and catalytic cracking $C_2^0$-$C_3^0$ of step (2).

The reaction conditions in steam cracking include a temperature of about 700° C.-1000° C., a residence time of about 0.05 s-0.6 s, and steam/oil ratio of about 0.1-1.0 by weight.

The reaction product vapor is separated to obtain $H_2$, $CH_4$, steam cracking $C_2^=$-$C_3^=$, steam cracking $C_2^0$-$C_3^0$, steam cracking $C_4$-$C_5$, steam cracking naphtha, fuel oil, wherein the steam cracking $C_2^=-C_3^=$ are a part of the desired products. The steam cracking $C_2^0-C_3^0$ are recycled to the steam cracking reactor and the steam cracked $C_4-C_5$ are recycled to the catalytic pyrolyzed reactor.

The above example process produces light olefins such as propylene, ethylene, etc, from heavy feedstocks by integrating process steps of hydrotreating, catalytic cracking, steam cracking, solvent extraction, etc. The yield of propylene exceeds 30%, and additionally results in production of aromatics, such as toluene, xylene, etc.

An example apparatus for producing light olefins includes a hydrotreating unit, wherein $H_2$, $CH_4$, hydrotreated $C_2^0-C_4^0$, hydrotreated naphtha, and hydrotreated product are obtained after the feedstock comes into contact with hydrogen and a hydrotreating catalyst.

(1) A catalytic cracking unit reacts the hydrotreated product with a catalytic cracking catalyst under the conditions of a reaction temperature between about 400° C. and 800° C. and a WHSV between about $0.1\,h^{-1}$-$750\,h^{-1}$ in at least two reaction zones, wherein the temperature of at least one reaction zone downstream of the first reaction zone is higher than that of the first reaction zone, and the WHSV of at least one reaction zone downstream of the first reaction zone is lower than that of the first reaction zone. The spent catalyst is separated from the reaction product vapor, the spent catalyst returning to all or a part of the reaction zones of step (2) after being regenerated by stripping and the reaction product vapor being separated to obtain $H_2$, $CH_4$, catalytic cracking $C_2^=-C_3^=$, catalytic cracking $C_2^0-C_3^0$, catalytic cracking $C_4-C_5$, catalytic cracking naphtha, light cycle oil, heavy cycle oil, wherein the $C_2^=-C_3^=$ are a part of the desired products and the $C_4-C_5$ are recycled to the catalytic cracking reactor.

(2) A steam cracking unit for reacting the hydrotreated $C_2^0-C_4^0$, hydrotreated naphtha, catalytic cracking $C_2^0-C_3^0$, and catalytic cracking $C_2^0-C_3^0$ with steam under a temperature between about 700° C. and 1000° C. The reaction product vapor is separated to obtain $H_2$, $CH_4$, steam cracking $C_2^=-C_3^=$, steam cracking $C_2^0-C_3^0$, steam cracking $C_4-C_5$, steam cracking naphtha, fuel oil, wherein the steam cracking $C_2^=-C_3^=$ are a part of the desired products.

(3) A selective hydrogenation unit selectively hydrogenates the catalytic cracking naphtha and steam cracking naphtha to obtain the selectively hydrotreated naphtha.

(4) A solvent extraction unit for extracting the selectively hydrotreated naphtha to obtain aromatics and extraction raffinate, wherein the aromatics are a part of the desired products and the extraction raffinate returns to step (3) as one of the feedstocks of steam cracking.

Figure 1:
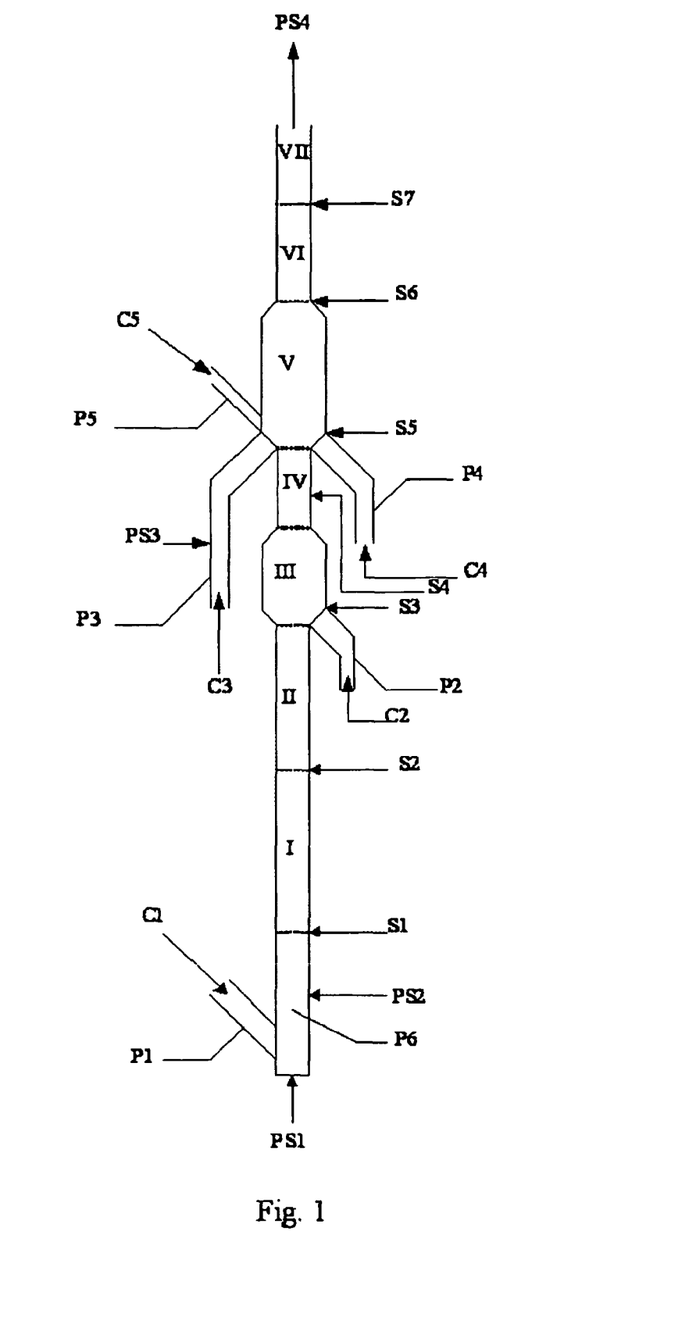
FIG. 1 is a schematic diagram of an example catalytic cracking process of technical scheme 1.

FIG. 1 illustrates a schematic diagram of the catalytic cracking process of technical scheme 1. There are 7 reaction zones, wherein the temperatures of both reaction zone III and reaction zone V are higher than that of reaction zone I, and the WHSVs of the reaction zones III and V are lower than that of reaction zone I. Medium PS2, such as propane, is injected from the pre-lifting section of the catalyst P6 at the bottom of reaction zone I to carry out reaction. This pre-lifting section P6 can also be regarded as a reaction zone.

In this example, the process flow is as follows:

Regenerated catalyst C1 from the regenerator enters pre-lifting section of the catalyst P6 at the bottom of reaction zone I through catalyst pipeline P1, reacts with medium PS2 after being lifted by medium PSI. In reaction zone I, feedstock S1 comes into contact with the catalyst and stream from pre-lifting section P6 and reacts under a reaction temperature between about 500° C. and 650° C., a WHSV between about $2\,h^{-1}$ and $300\,h^{-1}$ an catalyst/oil ratio between about 3 and 20 by weight, and a reaction pressure between about 0.12 MPa and 0.6 MPa (absolute pressure). The reaction product and catalyst then enter reaction zone II together.

In reaction zone II, the $C_4$ hydrocarbons feedstock S2 from other catalytic cracking unit comes into contact with the catalyst and stream from reaction zone I and reacts under a reaction temperature between about 490° C. and 640° C., a WHSV between about $20\,h^{-1}$ and $750\,h^{-1}$, an catalyst/oil ratio between about 3 and 20 by weight, and a reaction pressure between about 0.12 MPa and 0.6 MPa (absolute pressure). The reaction product and catalyst then enter reaction zone III together.

In reaction zone III, the $C_4$ hydrocarbons feedstock S3 from the present process comes into contact with the catalyst and stream from reaction zone II and the regenerated catalyst from pipeline P2 and reacts under a reaction temperature between about 510° C. and 660° C., a WHSV between about $2\,h^{-1}$ and $150\,h^{-1}$, an catalyst/oil ratio between about 3 and 20 by weight, and a reaction pressure between about 0.12 MPa and 0.6 MPa (absolute pressure). The reaction product and catalyst then enter reaction zone IV together.

In reaction zone IV, the $C_5$ hydrocarbons feedstock S4 from the present process comes into contact with the catalyst and stream from reaction zone III and reacts under a reaction temperature between about 490° C. and 640° C., a WHSV between about $20\,h^{-1}$ and $750\,h^{-1}$, an catalyst/oil ratio between 3 and 20 by weight, and a reaction pressure between about 0.12 MPa and 0.6 MPa (absolute pressure). The reaction product and catalyst then enter reaction zone V together.

In reaction zone V, a part of feedstock and $C_5$ hydrocarbons feedstock S5 from the present process come into contact and mix with the catalyst and stream from reaction zone IV, spent catalyst C5 from pipeline P5, regenerated catalyst C4 from pipeline P4, and the catalyst and reaction product after regenerated catalyst C3 from pipeline P3 contacts and reacts with propane PS3, and react under a reaction temperature between about 510° C. and 700° C., a WHSV between about $1\,h^{-1}$ and $100\,h^{-1}$, an catalyst/oil ratio between about 3 and 50 by weight, and a reaction pressure between about 0.12 MPa and 0.6 MPa (absolute pressure). The reaction product and catalyst then enter reaction zone VI together.

In reaction zone VI, $C_6$ feedstock S6 from the present process comes into contact and mixes with the catalyst and stream from reaction zone V and reacts under a reaction temperature between about 510° C. and 700° C., a WHSV between about $20\,h^{-1}$ and $700\,h^{-1}$, an catalyst/oil ratio between about 3 and 50 by weight, and a reaction pressure between about 0.12 MPa and 0.6 MPa (absolute pressure). The reaction product and catalyst then enter reaction zone VII together.

In reaction zone VII, water or steam S7 comes into contact and mixes with the catalyst and stream from reaction zone VI and reacts under a reaction temperature between about 450° C. and 700° C., a WHSV between about $20\,h^{-1}$ and $700\,h^{-1}$, an catalyst/oil ratio between about 3 and 50 by weight, and a reaction pressure between about 0.12 MPa and 0.6 MPa (absolute pressure). The reaction products vapor and catalyst PS4 then enter the catalyst/products vapor separation system. The separated product vapor enters the product vapor separation system and the catalyst enters the regenerator for generation optionally after being stripped.

Figure 2:
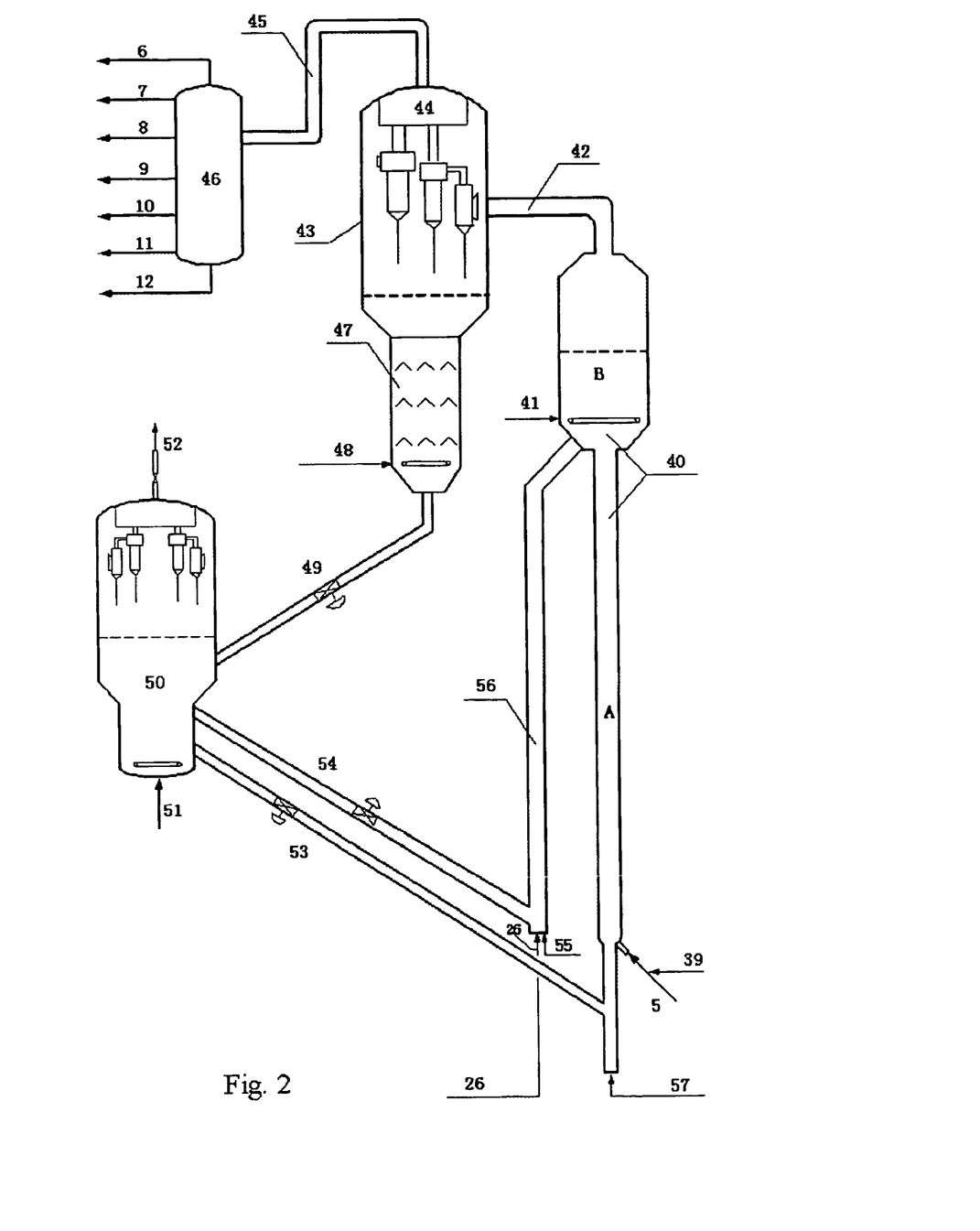
FIG. 2 is a schematic diagram of an example catalytic cracking process of technical scheme 1.

FIG. 2 illustrates a schematic diagram of an example catalytic cracking process of technical scheme 1.

In this process, the catalytic cracking reactor 40 includes the first reaction zone, i.e. riser A, the second reaction zone, i.e. fluidized bed B in series. The difference between the reaction temperature of the second reaction zone and that of the first reaction zone is about 10° C.-200° C., preferably about 20° C.-100° C., and the ratio of the WHSV of the second reaction zone to that of the first reaction zone is about 1:1.1-1:750, preferably about 1:1.1-1:300.

In one example, the process flow is as follows: The pre-lifting steam enters from the bottom of riser A through pipeline 57 and the regenerated catalyst move upward along riser A with increasing velocity under the pre-lifting action of the steam. The feedstock is injected into riser A through pipeline 5 together with atomizing steam from pipeline 39 and comes into contact with the regenerated catalyst. After being lifted by the steam from pipeline 55, the regenerated catalyst from pipeline 54 enters the vertical transfer line 56 together with $C_2^0$-$C_3^0$ and $C_4$-$C_8$ from pipeline 26 and moves upward, and finally enters fluidized bed B to carry out reaction together with the product vapor and catalyst from riser A.

Steam enters the bottom of fluidized bed B through pipeline 41 to ensure the fluidization and reaction of fluidized bed B. The product vapor produced in fluidized bed B and the deactivated spent catalyst enter the cyclone in disengager 43 through pipeline 42 to carry out the separation of the spent catalyst from the product vapor. The product vapor enters collection chamber 44 and the catalyst fine powder returns to the disengager through the leg. The spent catalyst in the disengager flows towards stripping section 47 and comes into contact with the steam from pipeline 48. The product vapor stripped from the spent catalyst enters chamber 44 through the cyclone. The spent catalyst after stripping enters regenerator 50 through sloped pipe 49. The main air enters the regenerator through pipeline 51 to burn off coke on the spent catalyst and regenerate the deactivated spent catalyst, and the stack gas enters the fume machine through pipeline 52.

The regenerated catalyst is divided into two parts, wherein one part enters riser A through sloped pipe 53 and the other part enters fluidized bed B sequentially through sloped pipe 54 and vertical transfer line 56 for recycle use. The product vapor in chamber 44 enter subsequent separation system 46 through pipeline 45, wherefrom the ethylene and propylene obtained through separation are withdrawn through pipeline 7, the catalytic cracking dry gas (i.e. hydrogen and methane) is withdrawn through pipeline 6, the catalytic cracking $C_2^0$-$C_3^0$ is withdrawn through pipeline 8 and finally introduced into vertical transfer line 56 through pipeline 26, the catalytic cracking $C_4$-$C_5$ is withdrawn through pipeline 9, the catalytic cracking naphtha is withdrawn through pipeline 10 to separate aromatics such as toluene, xylene, etc, the catalytic cracking diesel is withdrawn through pipeline 11, the diesel or hydrotreated diesel, the catalytic cracking cycle oil and slurry are withdrawn through pipeline 12. The catalytic cracking $C_4$-$C_5$ returns to fluidized bed B sequentially through pipeline 26 and vertical transfer line 56. The diesel or hydrotreated diesel, catalytic cracking cycle oil, and slurry returns to riser A together through pipeline 5.

Figure 3:
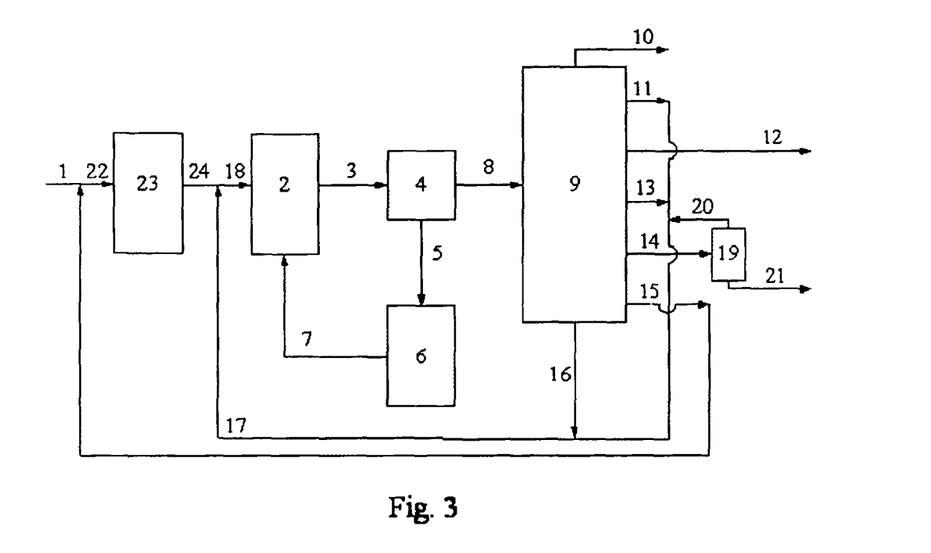
FIG. 3 is a schematic example flowsheet of the process of technical scheme 2.

FIG. 3 illustrates a schematic example flowsheet of the process of technical scheme 2. In this example, the feedstock mixes through pipeline 1 with the cycle oil from pipeline 15, enters hydrotreating unit 23 through pipeline 22, comes into contact with the hydrotreating catalyst and hydrogen, and reacts under the conditions of a hydrogen partial pressure between about 3.0 MPa and 20.0 MPa, a reaction temperature between about 300° C. and 450° C., a hydrogen/oil ratio between about 300 and 2000 by volume, and a LHSV between about 0.1 h$^{-1}$ and 3.0 h$^{-1}$. The oil produced in the hydrotreating unit mixes through pipeline 24 with the recycle stream from pipeline 17, then enters catalytic cracking reactor 2, comes into contact with catalytic cracking and steam, and reacts under the conditions of a temperature between about 500° C. and 700° C., a pressure between about 0.15-0.4 MPa (absolute pressure), a ratio of the catalytic cracking catalyst to catalytic cracking feedstock between about 5 and 50 by weight, a ratio of steam to catalytic cracking feedstock between 0.05 and 1.0 by weight. The coked spent catalyst and reaction product vapor enters catalyst/oil separator 4 through pipeline 3, the separated spent catalyst enters regenerator 6 through pipeline 5.

The catalyst regenerated by burning off coke possesses higher activity and selectivity, which returns to reactor 2 through pipeline 7, and the reaction product vapor enters product separator 9. The separated ethylene and propylene are withdrawn through pipeline 12, and the cracked naphtha from which $C_5$-$C_6$ is removed enters solvent extraction unit 19. The obtained aromatics are withdrawn through pipeline 21, hydrogen and methane are withdrawn through pipeline 10, ethane and propane are withdrawn through pipeline 11, $C_4$-$C_6$ are withdrawn through pipeline 13, the cycle oil is withdrawn through pipeline 15, and the slurry is withdrawn through pipeline 16. Ethane and propane, $C_4$-$C_6$, the extraction raffinate of naphtha, and slurry are all or partly return to catalytic cracking reactor 2 sequentially through pipelines 17 and 18, and the cycle oil return to hydrotreating unit 23 sequentially through pipelines 15 and 22.

Figure 4:
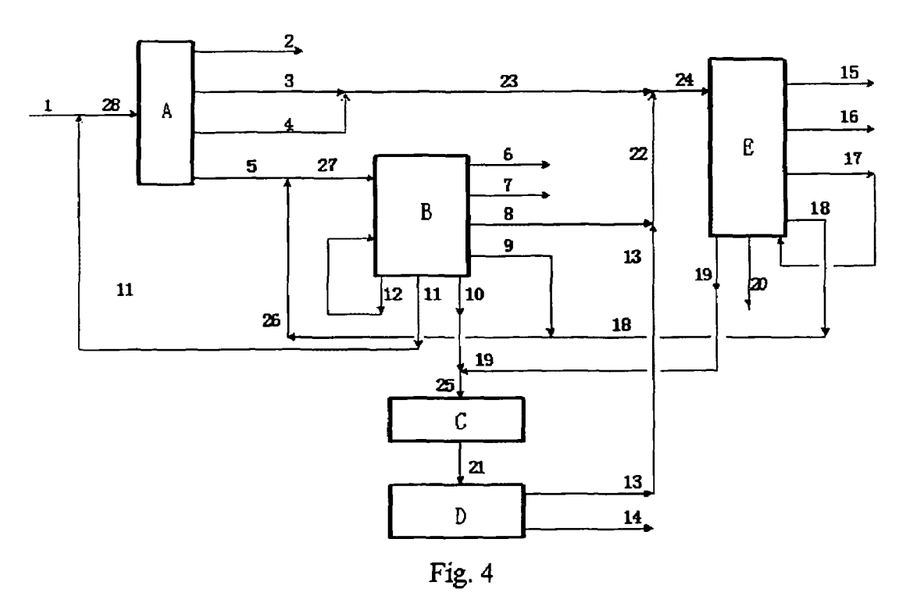
FIG. 4 is a schematic example flowsheet of the process and apparatus of technical scheme 3.

FIG. 4 illustrates a schematic example flowsheet of the process and apparatus of technical scheme 3.

In this example, feedstock mixes through pipeline 1 with diesel from pipeline 11 then enters hydrogenation unit A. $H_2$, $CH_4$, hydrotreated $C_2^0$-$C_4^0$, hydrotreated naphtha, and hydrotreated product obtained by hydrotreating are withdrawn from pipelines 2, 3, 4, and 5 respectively. The hydrotreated $C_2^0$-$C_4^0$ and hydrotreated naphtha mixes respectively through pipelines 3 and 4 then enters steam cracking unit E sequentially through pipelines 23 and 24. The hydrotreated product as a feedstock for catalytic cracking mixes with $C_4$-$C_5$ from pipeline 26, enters catalytic cracking unit B and reacts under the conditions of a temperature between about 500° C. and 700° C., a pressure between about 0.15-0.4 MPa (absolute pressure), a ratio of the catalytic cracking catalyst to catalytic cracking feedstock between about 5 and 50 by weight, a ratio of steam to catalytic cracking feedstock between about 0.05 and 1.0 by weight. $H_2$, $CH_4$, catalytic cracking $C_2^=$-$C_3^=$, catalytic cracking $C_2^0$-$C_3^0$, catalytic cracking $C_4$-$C_5$, catalytic cracking naphtha, diesel, cycle oil obtained in catalytic cracking unit B are withdrawn from pipelines 2, 3, 4, and 5 respectively. $C_2^=$-$C_3^=$ is one of the desired product.

The $C_2^0$-$C_3^0$ as one of the steam cracking feedstocks enters steam cracking unit E sequentially through pipelines 8, 22, and 24. The catalytic cracking $C_4$-$C_5$ mixes through pipeline 9 with steam cracking $C_4$-$C_5$ from pipeline 18 then returns to catalytic cracking unit B sequentially through pipelines 26 and 27. The catalytic cracking naphtha mixes with steam cracking naphtha from pipeline 19 then enters selective hydrogenation unit C through pipeline 25. The diesel returns to hydrogenation unit A sequentially through pipelines 11 and 28. The cycle oil returns to catalytic cracking unit B through pipeline 12. The stream from selective hydrogenation unit C enters solvent extraction unit D. The BTX obtained in solvent extraction unit D are withdrawn from pipeline 14 as desired products, and the extraction raffinate enters steam cracking unit E sequentially through pipelines 13, 22, and 24.

The hydrotreated $C_2^0$-$C_4^0$, hydrotreated naphtha, catalytic cracking $C_2^0$-$C_3^0$, and extraction raffinate first mix respectively through pipelines 3, 4, 8, and 13, and then enter steam cracking unit E through pipeline 24. $H_2$, $CH_4$, steam cracked $C_2^=-C_3^=$, steam cracked $C_2^0-C_3^0$, steam cracked $C_4-C_5$, steam cracked naphtha, and fuel oil are withdrawn respectively through pipelines 15, 16, 17, 18, 19, and 20, wherein the steam cracked $C_2^=-C_3^=$ is withdrawn from the unit through pipeline 16 as one of the desired products, the steam cracked $C_2^0-C_3^0$ returns to steam cracking unit E through pipeline 17, the steam cracked $C_4-C_5$ enters catalytic cracking unit B sequentially through pipelines 18, 26, and 27, and the steam cracked naphtha enters selective hydrogenation unit C through pipeline 19.

The disclosed examples provide the benefit of increasing the yield of light olefins, such as propylene, ethylene, etc., wherein the yield of propylene exceeds 20% by weight, preferably exceeds 25%, and more preferably exceeds 30%. The examples processes can also produce joint products, aromatics rich in toluene, xylene, etc. Therefore, a technical breakthrough of the refinery concept is realized, i.e., a conversion of the refinery from conventional fuel and fuel-lubricant production mode into chemical industry mode, and a development and extension of the refinery from single oil refining to the production of downstream products with high added values. This conversion not only solves the problem of the shortage of the chemical feedstocks, but also increases the benefit of the refinery.

The following examples will further describe the present invention but not limit it.

The feedstock used in the examples is VGO, the properties are shown in Table 1, and the solvent used in the examples is sulfolane.

The process for preparing the catalytic cracking catalyst used in the examples is briefly described as follows:

1) 20 g of $NH_4Cl$ was dissolved in 1000 g of water, whereto 100 g (dry basis) of crystallized product ZRP-1 zeolite (produced in the Catalyst Plant of Qilu Petrochemicals Co., $SiO_2/Al_2O_3=30$, content of rare earths $RE_2O_3=4.0\%$ by weight) was added, and a filter cake was obtained after exchanging at 90° C. for 0.5 hour and filtration. The filter cake was impregnated with a solution of 4.0 g of $H_3PO_4$ (with a concentration of 85%) and 4.5 g of $Fe(NO_3)_3$ in 90 g of water and then dried. The resultant solid was calcined at 550° C. for 2 hours to obtain a intermediate pore size zeolite containing phosphor and iron and having the structure of MFI, the composition of which determined by element analysis was $0.1Na_2O.5.1Al_2O_3.2.4P_2O_5.1.5Fe_2O_3.3.8RE_2O_3.88.1SiO_2$.

2) 75.4 kg of halloysite (Product of Suzhou Porcelain Clay Co., solid content 71.6% by weight) was slurried with 250 kg of cation-removed water and 54.8 kg of pseudo-boehmite (industrial product of Shandong Alumina Plant, solid content 63% by weight) was added. PH is adjusted at 2-4 with hydrochloric acid, the slurry was uniformly stirred, and laid aside for aging at 60-70° C. for 1 hour. The temperature was lowered down to below 60° C. while maintaining the pH at 2-4, and then 4.5 kg of alumina sol (industrial product of Shandong Alumina Plant, $Al_2O_3$ content 21.7% by weight) was added. A mixed slurry was obtained after stirring for 40 minutes.

3) The intermediate pore size zeolite containing phosphor and iron and having the structure of MFI prepared in step 1) (dry basis 45 kg) and DASY zeolite (industrial product of the Catalyst Plant of Qilu Petrochemicals Co., unit cell size 2.445-2.448 nm, $RE_2O_3$ content 2.0%, dry basis 7.5 kg) were added to the mixed slurry obtained in step 2) and uniformly stirred. The resulted slurry was shaped by spray drying, and the product was washed with a solution of ammonium dihydrogen phosphate (phosphor content 1% by weight) to remove free $Na^+$. After drying, a sample of the catalytic cracking catalyst was obtained. The composition of the catalyst was 30% by weight of MFI structure intermediate pore size zeolite containing phosphor and iron, 5% by weight of DASY zeolite, 23% by weight of pseudo-boehmite, 6% by weight of alumina sol, and balanced kaolin.

The process for preparing the hydrotreating catalyst used in the examples is briefly described as follows. Ammonium metatungstate (($NH_4)_4W_4O_{13}.18H_2O$, chemically pure) and nickel nitrate ($Ni(NO_3)_2.6H_2O$, chemically pure) were dissolved in water to prepare 200 ml of solution. 50 g of alumina support was added to the solution and impregnated at room temperature for 3 hours. During impregnation, the impregnating solution was treated with an ultrasonic instrument for 30 min, and then cooled, filtered and dried in a microwave oven for about 15 min. The composition of the catalyst was 30% by weight of $WO_3$, 3.1% by weight of NiO, and balanced Alumina.

The process for preparing the hydrotreating catalyst used in the examples is briefly described as follows. Ammonium metatungstate (($NH_4)_4W_4O_{13}.18H_2O$, chemically pure) and nickel nitrate ($Ni(NO_3)_2.6H_2O$, chemically pure) were dissolved in water to prepare 200 mL of solution. 100 g of alumina support was added to the solution and impregnated at room temperature for 4 hours. After separation, the wet catalyst was dried in an oven for 4 hours and calcined in a tube furnace with blowing air at 500° C. for 4 hours. The composition of the catalyst was 25.3% by weight of $WO_3$, 2.3% by weight of NiO, and balanced alumina.

Example 1

The experiment of the present example was carried out according to the flow in FIG. 1. Feedstock A was directly used as the feedstock of catalytic cracking and the experiment was carried out in seven reaction zones consisting of risers and fluidized beds. The reaction temperatures of reaction zones I, II, III, IV, V, VI, and VII sequentially were 530° C., 520° C., 550° C., 540° C., 640° C., 620° C., and 580° C., and the WHSVs of reaction zones I, II, III, IV, V, VI, and VII sequentially were 360 $h^{-1}$, 720 $h^{-1}$, 20 $h^{-1}$, 180 $h^{-1}$, 5 $h^{-1}$, 200 $h^{-1}$, and 620 $h^{-1}$, wherein the reaction temperatures of reaction zones III and V were 20° C. and 110° C. higher than that of reaction zone I respectively, the ratio of WHSVs of reaction zones III and V (fluidized bed) to that of reaction zone I (riser) were 1:18 and 1:72 respectively, and the heats supplemented to reaction zones III and V account for 11% and 60% of the reaction heat of the total reaction system respectively. Finally, the products were separated, wherein $C_3-C_5$ was cycled to the fluidized beds. The operating conditions of reaction zones I, III, and V, and product distribution are shown in Table 2.

It can be seen from Table 2 that the yields of propylene and ethylene attain as high as 35.21% and 14.56% by weight respectively, and those of toluene and xylene are 3.95% and 4.26% by weight respectively.

Example 2

The experiment of the present example was carried out according to the flow in FIG. 2. Feedstock B was directly used as the feedstock of catalytic cracking and the experiment was carried out in a medium-sized riser plus a fluidized bed reactor, wherein the reaction temperature of the fluidized bed was 30° C. higher than that of the riser, the ratio of the WHSV of the fluidized bed to that of the riser was 1:360, and the heat supplemented to the fluidized bed account for 22% of the reaction heat of the total reaction system. Finally, the products were separated, wherein only the slurry was cycled to the riser and $C_4$-$C_6$ was cycled to the fluidized bed, but the other stream were not cycled. The operating conditions of catalytic cracking and product distribution are shown in Table 2.

It can be seen from Table 2 that the yields of propylene and ethylene are as high as 30.46% and 18.31% by weight respectively, and those of toluene and xylene are 2.45% and 7.38% by weight respectively.

Example 3

The experiment of the present example was carried out according to the flow in FIG. 3. Feedstock A was first subjected to hydrotreating, and the hydrotreated product (the content of hydrogen increased from 12.40% to 13.54% by weight and the content of aromatics decreased from 44.1% to 20.0% by weight) was used as the feedstock of catalytic cracking. The experiment was carried out in a medium-sized riser plus a fluidized bed reactor, wherein the reaction temperature of the fluidized bed was 40° C. higher than that of the riser, the ratio of the WHSV of the fluidized bed to that of the riser was 1:30, and the heat supplemented to the fluidized bed account for 25% of the reaction heat of the total reaction system. Finally, the products were separated, wherein only the slurry was cycled to the riser, but the other stream was not cycled. The operating conditions of hydrotreating and catalytic cracking and product distribution are shown in Table 3.

It can be seen from Table 3 that the yields of propylene and ethylene are as high as 32.97% and 12.63% by weight respectively, and those of toluene and xylene are 1.93% and 4.05% by weight respectively.

Example 4

The experiment of the present example was carried out according to the flow in FIG. 4. The reactor for catalytic cracking is a riser plus a fluidized bed reactor in a pilot plant, wherein the reaction temperature of the fluidized bed was 40° C. higher than that of the riser, the ratio of the WHSV of the fluidized bed to that of the riser was 1:30, and the heat supplemented to the fluidized bed account for 30% of the reaction heat of the total reaction system. Finally, the products were separated, wherein only the slurry was cycled to the riser, but the other stream was not cycled. All the hydrotreating, catalytic cracking, selective hydrogenation and solvent extraction experiments were carried out in corresponding middle-sized units.

The feedstock used in the present example was the same as that in Example 3, i.e. feedstock A, and the operating conditions and product distribution are shown in Table 3. It can be seen from Table 3 that the yields of propylene and ethylene are as high as 40.65% and 20.64% by weight respectively, and those of toluene and $C_8$ aromatics are 4.34% and 5.18% by weight respectively.

TABLE 1

| No. of feedstock | Examples 1, 3, 4<br>A | Example 2<br>B |
|---|---|---|
| Property of feedstock | | |
| Density (20° C.), g/cm³ | 0.8886 | 0.9134 |
| Sulfur content, ppm | 4700 | 5800 |
| Nitrogen content, ppm | 1600 | 2900 |

TABLE 1-continued

| No. of feedstock | Examples 1, 3, 4<br>A | Example 2<br>B |
|---|---|---|
| Aromatics, m % | 26.3 | 32.6 |
| C, m % | 86.46 | 86.23 |
| H, m % | 12.86 | 12.69 |
| Boiling range (ASTM D-1160), ° C. | | |
| IBP | 312 | 327 |
| 10% | 361 | 363 |
| 30% | 412 | 409 |
| 50% | 452 | 450 |
| 70% | 478 | 482 |
| 90% | 506 | 504 |
| 95% | 532 | 526 |
| FBP | 546 | 542 |

TABLE 2

| No. of feedstock | Example 1<br>A | Example 2<br>B | Example 3<br>A |
|---|---|---|---|
| Hydrotreating unit Operation condition | | | |
| Reaction temperature, ° C. | — | — | 370 |
| Hydrogen partial pressure, MPa | — | — | 14.0 |
| LHSV, h⁻¹ | — | — | 0.6 |
| Hydrogen/oil ratio, v/v | — | — | 800 |
| Product distribution, m % | | | |
| Gas | — | — | 2.55 |
| Naphtha | — | — | 1.80 |
| Hydrotreated product | — | — | 96.90 |
| Catalytic cracking unit Operation condition | | | |
| Riser | reaction zone I | | |
| Reaction temperature, ° C. | 530 | 650 | 580 |
| Catalyst/oil ratio, m/m | 8 | 20 | 12 |
| WHSV, h⁻¹ | 360 | 180 | 120 |
| Steam injected (to feed), m % | 20 | 10 | 15 |
| Fluidized bed | reaction zone III/V | | |
| Reaction Temperature, ° C. | 550/640 | 680 | 620 |
| Catalyst/oil ratio, m/m | 10/30 | 45 | 25 |
| WHSV, h⁻¹ | 20/5 | 0.5 | 4 |
| Water injected (to feed), m % | 20/25 | 60 | 30 |
| Temperature difference between riser and the bed, ° C. | 20/110 | 30 | 40 |
| WHSV ratio (the fluidized bed/riser) | 1:18/1:72 | 1:360 | 1:30 |
| Product distribution, m % | | | |
| H₂ & CH₄ | 5.46 | 6.47 | 4.36 |
| Ethylene | 14.56 | 18.31 | 12.63 |
| Propylene | 35.21 | 30.46 | 32.97 |
| Ethane & propane | 4.23 | 5.17 | 4.73 |
| C₄ | 4.54 | 0 | 18.68 |
| C₅-C₆ | 2.53 | 0 | 1.86 |
| Toluene | 3.95 | 2.45 | 1.93 |
| Xylene | 4.26 | 7.38 | 4.05 |
| Other single-ring aromatics | 2.78 | 9.76 | 3.86 |
| Extraction raffinate of pyrolyzed naphtha | 5.59 | 1.84 | 1.09 |
| Cycle oil | 7.04 | 8.68 | 3.50 |
| Slurry | 0 | 0 | 2.28 |
| Coke | 9.85 | 9.48 | 8.06 |

TABLE 3

|  | Example 4 |
|---|---|
| Hydrotreating unit | |
| Reaction temperature, °C. | 370 |
| Hydrogen partial pressure, MPa | 14.0 |
| LHSV, h$^{-1}$ | 0.6 |
| H$_2$/oil ratio, v/v | 800 |
| Catalytic cracking unit | |
| Riser | |
| Reaction temperature, °C. | 580 |
| Catalyst/oil ratio, m/m | 12 |
| WHSV, h$^{-1}$ | 120 |
| Water injected (ratio to feed), m % | 15 |
| Fluidized bed | |
| Reaction temperature, °C. | 620 |
| Catalyst/oil ratio, m/m | 25 |
| WHSV, h$^{-1}$ | 4 |
| Water injected (ratio to feed), m % | 30 |
| Temperature difference between the fluidized bed/riser, °C. | 40 |
| WHSV ratio (the fluidized bed/riser) | 1:30 |
| Selective hydrogenation unit | |
| Reaction temperature, °C. | 200 |
| Hydrogen partial pressure, MPa | 4.0 |
| LHSV, h$^{-1}$ | 2.5 |
| Hydrogen/oil ratio, v/v | 350 |
| Solvent extraction unit | |
| Temperature, °C. | 90 |
| Solvent ratio, v/v | 3.5 |
| Yield of product, m % | |
| Methane & hydrogen | 8.60 |
| Ethylene | 20.64 |
| Propylene | 40.65 |
| Benzene | 1.28 |
| Toluene | 4.34 |
| C$_8$ aromatics | 5.18 |
| C$_9^+$ heavy aromatics | 6.03 |
| Fuel oil | 2.5 |
| Coke | 10.78 |

Although a preferred embodiment of this invention has been disclosed, a worker of ordinary skill in this art would recognize that certain modifications would come within the scope of this invention. For that reason, the following claims should be studied to determine the true scope and content of this invention.

The invention claimed is:

1. A process for producing light olefins and aromatics, comprising the steps of:
   obtaining a reaction system comprising a first reaction zone, a final reaction zone, and optionally one or more reaction zones disposed between the first reaction zone and the final reaction zone;
   introducing a feedstock and a catalytic cracking catalyst into the first reaction zone;
   introducing substantially all effluent from the first reaction zone into a reaction zone downstream from the first reaction zone;
   obtaining a spent catalyst and a reaction product stream from the final reaction zone;
   separating the spent catalyst from the reaction product stream;
   regenerating the spent catalyst to produce a regenerated catalyst;
   introducing the regenerated catalyst into the reaction system,
   wherein reaction temperatures in the reaction system range from 400° C. to 800° C. and a reaction temperature in a reaction zone downstream from the first reaction zone is higher than that of the first reaction zone,
   wherein values of WHSV in the reaction system range from 0.1 h$^{-1}$ and 750 h$^{-1}$ and the WHSV of a reaction zone downstream from the first reaction zone is lower than that of the first reaction zone.

2. The process according to claim 1, wherein the feedstock having a boiling range within the range of 25° C.-1200° C.

3. The process according to claim 1, wherein the reaction system comprises a second reaction zone, and effluent from the first reaction zone enters the second reaction zone.

4. The process according to claim 3, wherein the reaction system comprises a third reaction zone, and effluent from the second reaction zone enters the third reaction zone.

5. The process according to claim 1, wherein a difference between the reaction temperature in one reaction zone downstream from the first reaction zone and that of the first reaction zone ranges from about 20° C. to about 100° C., and a ratio of the WHSV in one reaction zone downstream from the first reaction zone to that of the first reaction zone ranges from about 1:1.1 to about 1:300.

6. The process according to claim 1, wherein a heat source for one reaction zone downstream from the first reaction zone is selected from the group consisting of a hot regenerated catalyst, a hot coke deposited catalyst, a hot fresh catalyst, one or more heating coil tubes, and combinations thereof.

7. The process according to claim 6, wherein an amount of heat supplied by the heat source accounts for 10%-80% of a reaction heat of the reaction system.

8. The process according to claim 6, wherein an amount of heat supplied by the heat source accounts for about 20%-60% of a reaction heat of the reaction system.

9. The process according to claim 1, wherein the reaction system has a reaction temperature of about 500° C. to about 700° C., a WHSV of about 1 h$^{-1}$ to about 500 h$^{-1}$, a reaction pressure of about 0.10 MPa to about 1.0 MPa, and a ratio of the regenerated catalyst to the feedstock of about 1 to about 150 by weight.

10. The process according to claim 1, wherein each of the reaction zones in the reaction system is selected from a riser, a fluidized bed, an ascending transfer line, a descending transfer line, and a moving bed.

11. The process according to claim 1, wherein the feedstock is petroleum hydrocarbons, other mineral oils, or combinations thereof, wherein the petroleum hydrocarbon is one selected from a group consisting of vacuum gas oil, atmospheric gas oil, coked gas oil, deasphalted oil, vacuum residuum, atmospheric residuum, cycle oil, slurry, diesel, naphtha, hydrocarbons with 4-8 carbon atoms, alkanes with 2-3 carbon atoms, or mixtures thereof, and the other mineral oil is selected from liquid products from coal liquefaction, tar sand oil, shale oil, or mixtures thereof.

12. The process according to claim 11, wherein said vacuum gas oil, atmospheric gas oil, coked gas oil, deasphalted oil, vacuum residuum, atmospheric residuum, diesel, and naphtha are one of whole fraction and partial fraction.

13. The process according to claim 11, wherein said naphtha is selected from the group consisting of catalytic cracking naphtha, straight-run naphtha, coked naphtha, steam cracking naphtha, thermal cracking naphtha, hydrotreated naphtha, and mixtures thereof.

14. The process according to claim 11, wherein said diesel is selected from the group consisting of catalytic cracking light cycle oil (LCO), straight-run diesel, coked diesel, thermal cracking diesel, hydrotreated diesel, and mixtures thereof.

15. The process according to claim 1, wherein the feedstock of the first reaction zone is selected from the group consisting of vacuum gas oil, atmospheric gas oil, coked gas oil, deasphalted oil, vacuum residuum, atmospheric residuum, cycle oil, slurry, and mixtures thereof.

16. The process according to claim 1, wherein the feedstock of one reaction zone downstream from the first reaction zone is selected from the group consisting of diesel, naphtha, hydrocarbons with 4-8 carbon atoms, alkanes with 2-3 carbon atoms, and mixtures thereof.

17. The process according to claim 1, wherein said catalytic cracking catalyst comprises about 10% to about 50% zeolite by weight, about 5% to about 90% inorganic oxide by weight, and about 0% to about 70% clay by weight.

18. The process according to claim 17, wherein said zeolite includes a first zeolite having in intermediate pore size and a second zeolite having a relatively larger pore size, wherein the first zeolite accounts for about 25% to about 100% of the total weight of the zeolite and the second zeolite accounts for about 0% to about 75% by weight of the total weight of the zeolite; the first zeolite is selected from ZSM series zeolites and ZRP zeolites, and the ZSM series zeolite is one selected from the group consisting of ZSM-5, ZSM-11, ZSM-12, ZSM-23, ZSM-35, ZSM-38, ZSM-48, and mixtures thereof; and the second zeolite is one selected from the group consisting of rare earth Y, rare earth HY, ultrastable Y, high silica Y, and mixtures thereof.

19. The process according to claim 17, wherein said inorganic oxide is selected from $SiO_2$ and $Al_2O_3$, and the clay is selected from kaolin clay and halloysite.

20. The process according to claim 1, wherein the reaction product stream comprises ethylene, propylene, and butene.

21. The process according to claim 1, wherein a yield of propylene in the reaction product stream is greater than 30%.

* * * * *